US006723751B1

(12) United States Patent
Englert et al.

(10) Patent No.: US 6,723,751 B1
(45) Date of Patent: Apr. 20, 2004

(54) CRYSTALLINE FORMS OF THE SODIUM SALT OF 5-CHLORO-2-METHOXY-N-(2-(4-METHOXY-3-METHYLAMINOTHIO-CARBONYLAMINOSULFONYLPENYL) ETHYL)BENZAMIDE

(75) Inventors: Heinrich Christian Englert, Hofheim (DE); Uwe Gerlach, Hattersheim (DE); Harald Schneider, Offenbach am Main (DE); Tobias Metzenthin, Frankfurt (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/549,538

(22) Filed: Apr. 14, 2000

(30) Foreign Application Priority Data

Apr. 16, 1999 (DE) .......................................... 199 17 233

(51) Int. Cl.[7] ........................ A61K 31/17; C07C 303/14
(52) U.S. Cl. ......................................... 514/584; 564/23
(58) Field of Search ............................. 564/23; 514/584

(56) References Cited

U.S. PATENT DOCUMENTS

| 5,574,069 A | 11/1996 | Englert et al. ............... 514/586 |
| 5,698,596 A | 12/1997 | Englert et al. ............... 514/586 |
| 5,776,980 A | 7/1998 | Englert et al. ............... 514/586 |

FOREIGN PATENT DOCUMENTS

| EP | 0 612 724 A1 | 8/1994 |
| WO | WO 00/15204 | 3/2000 |

*Primary Examiner*—Peter O'Sullivan
(74) *Attorney, Agent, or Firm*—Finnegan, Henderson, Farabow, Garrett & Dunner, L.L.P.

(57) ABSTRACT

The present invention relates to crystalline forms of the sodium salt of 5-chloro-2-methoxy-N-(2-(4-methoxy-3-methylaminothiocarbonylaminosulfonylphenyl)ethyl) benzamide, processes for their preparation, their use, and pharmaceutical preparations comprising them.

28 Claims, 4 Drawing Sheets

Figure 1:
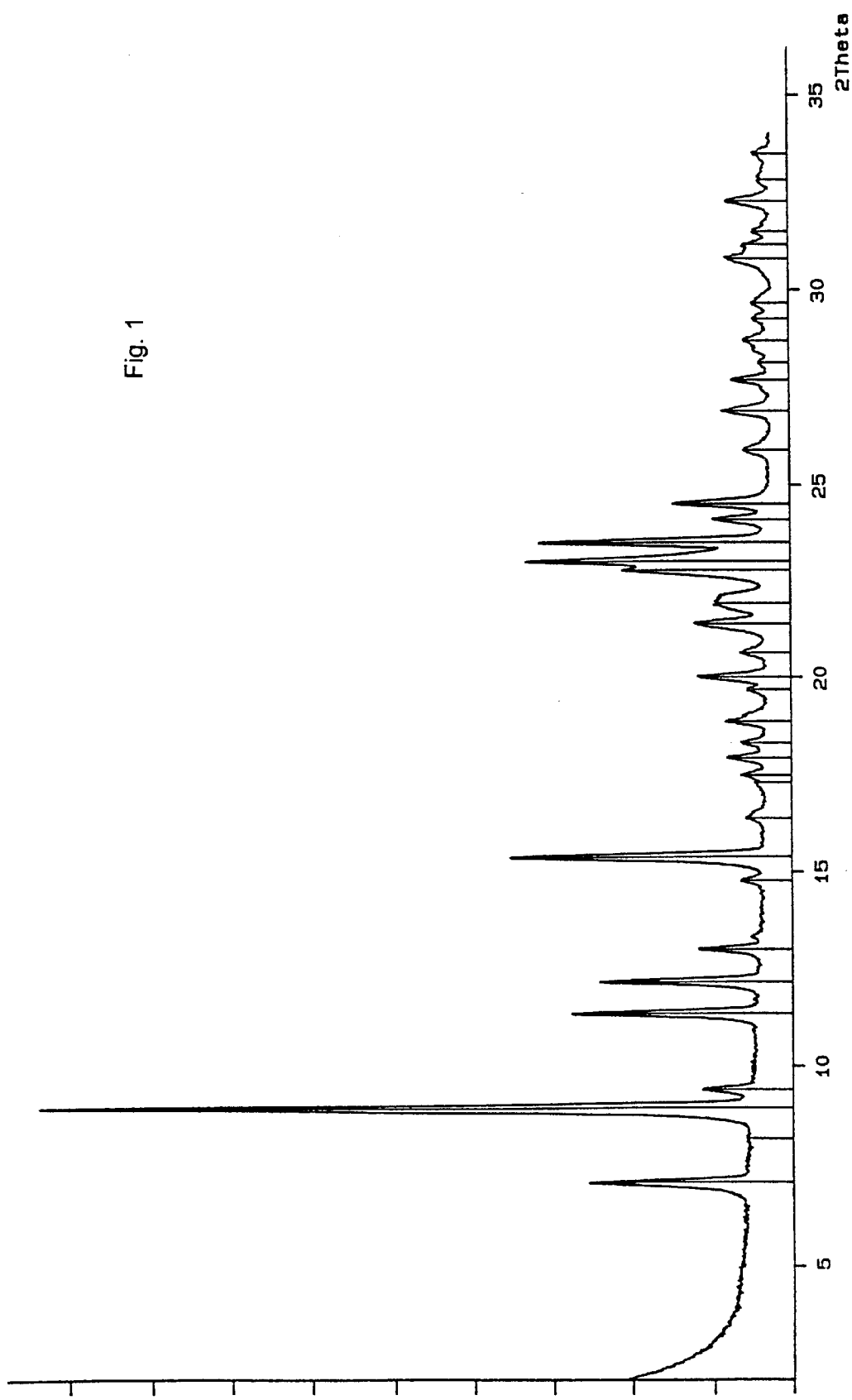
Figure 2:
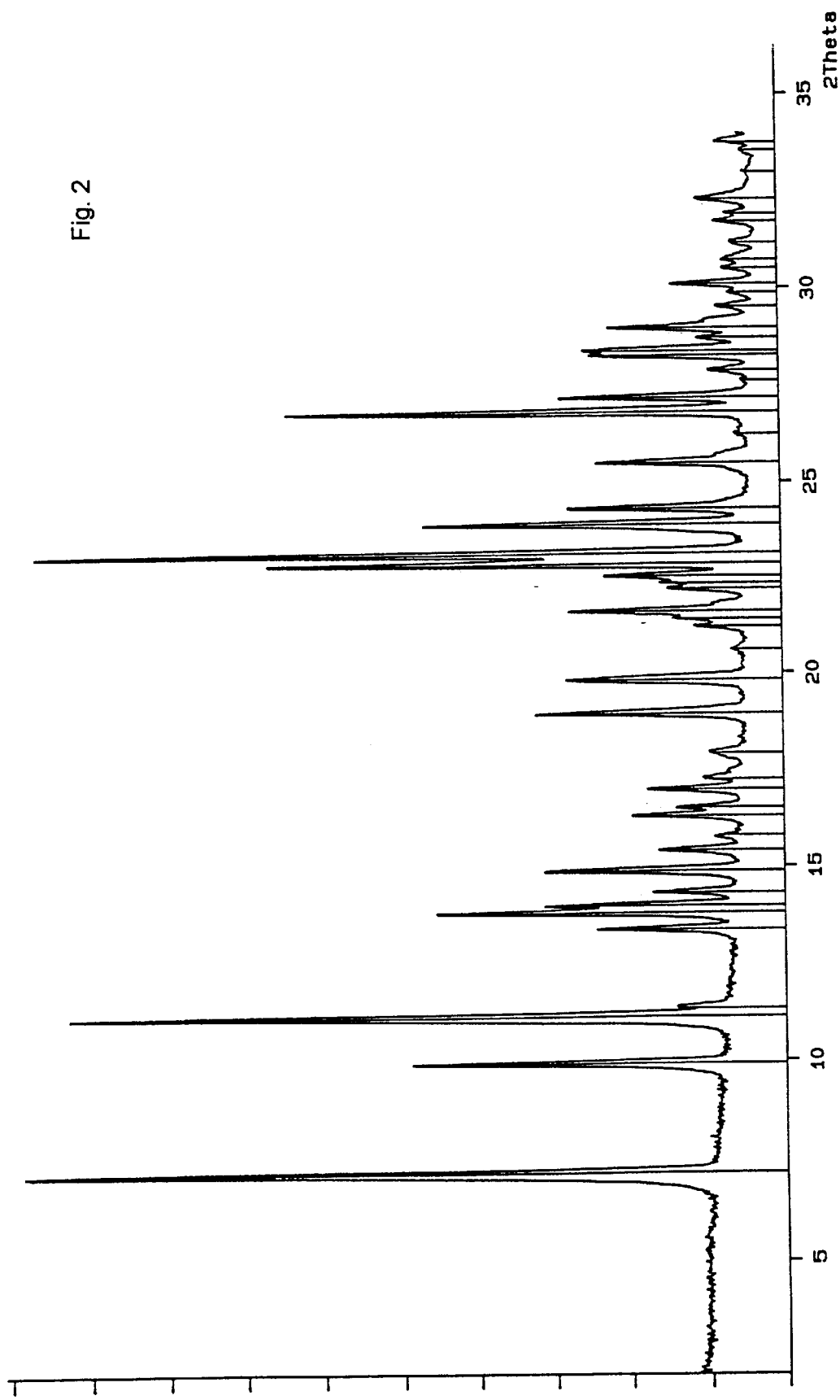
Figure 3:
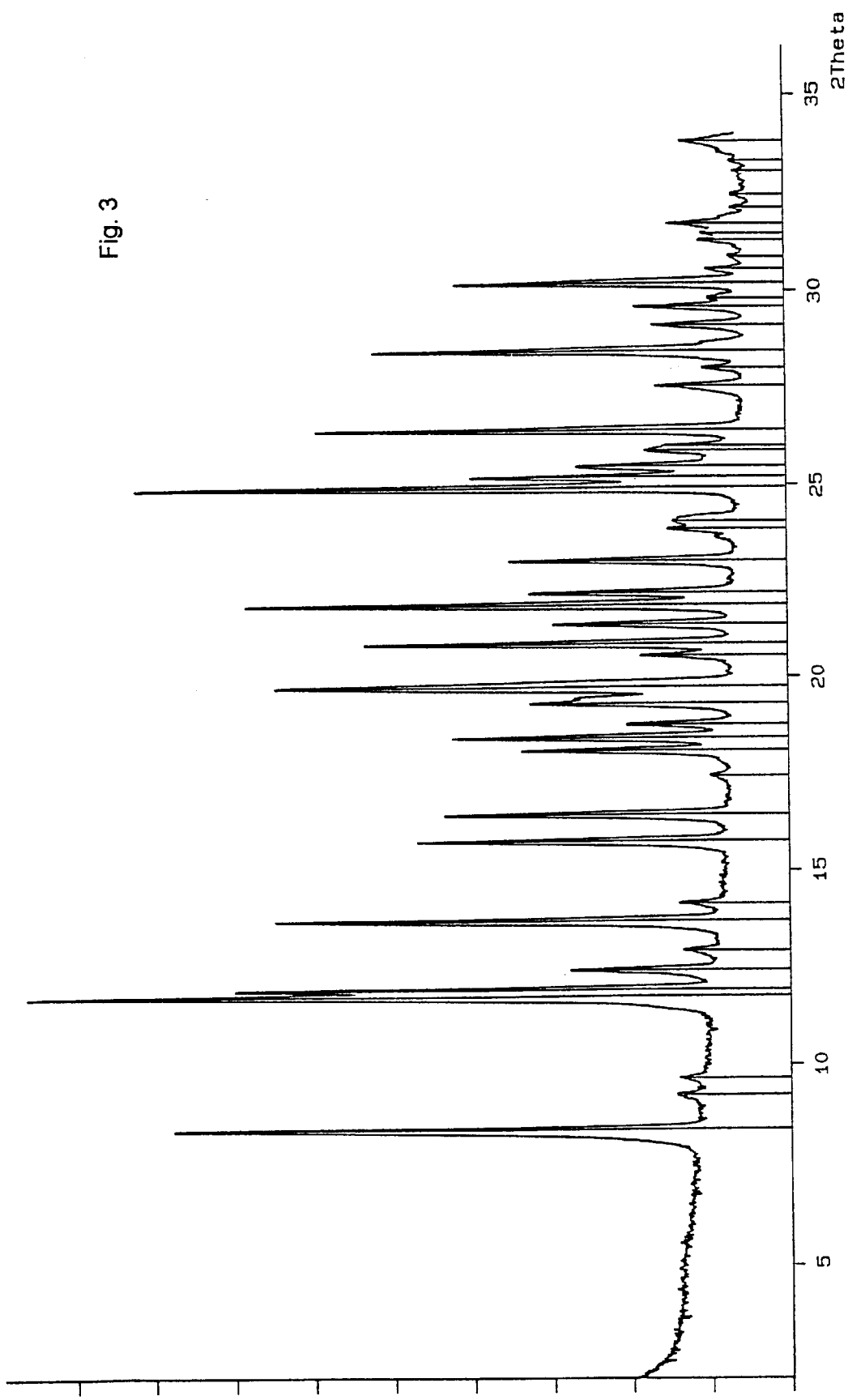
Figure 4:
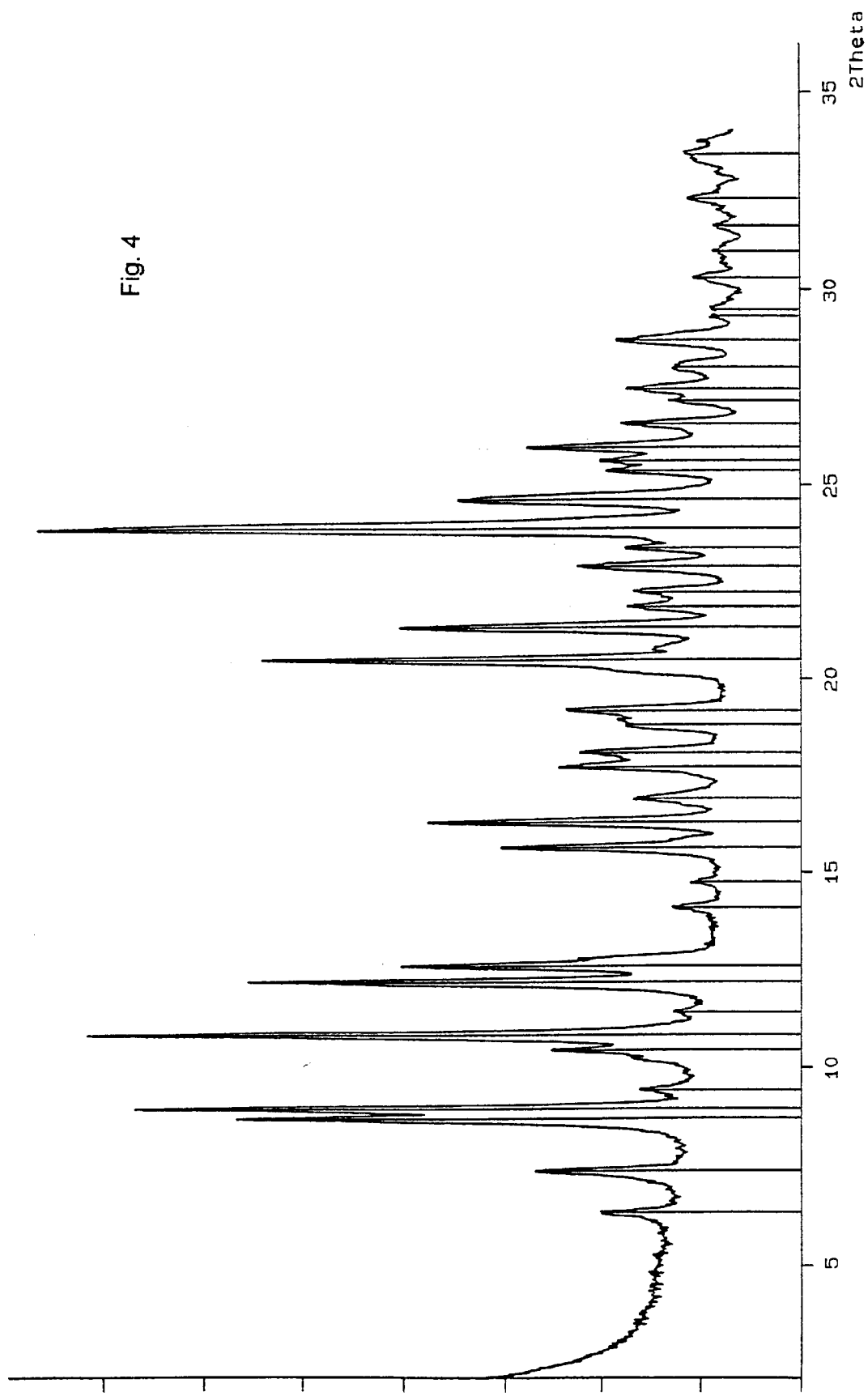

CRYSTALLINE FORMS OF THE SODIUM SALT OF 5-CHLORO-2-METHOXY-N-(2-(4-METHOXY-3-METHYLAMINOTHIO-CARBONYLAMINOSULFONYLPENYL) ETHYL)BENZAMIDE

The present invention relates to novel crystalline forms of the sodium salt of 5-chloro-2-methoxy-N-(2-(4-methoxy-3-methylaminothiocarbonylaminosulfonylphenyl)ethyl) benzamide, processes for their preparation, their use, and pharmaceutical preparations comprising them.

5-Chloro-2-methoxy-N-(2-(4-methoxy-3-methylaminothiocarbonylaminosulfonylphenyl)ethyl) benzamide of formula I,

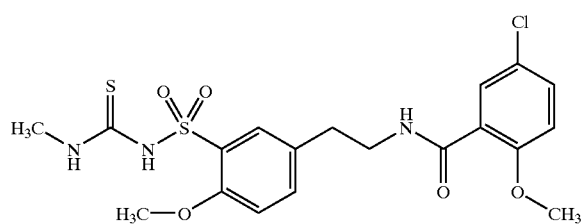

I also abbreviated below as "benzamide I", is described, for example, in U.S. Pat. Nos. 5,574,069 and 5,776,980 and corresponding publications, for example EP-A-612 724, which are incorporated herein by reference and whose contents are explicitly part of the present disclosure. The benzamide I has valuable pharmacological properties. It inhibits ATP-sensitive potassium channels and prolongs or normalizes a shortened action potential of heart muscle cells, as can occur in ischemic conditions of the heart, without causing a marked depolarization of the cell membrane of β-cells of the pancreas and a hypoglycemic action. The benzamide I and its physiologically tolerable salts are suitable as pharmaceutical active compounds for the prevention and treatment of various disease states, for example of cardiac arrhythmias such as ventricular fibrillation, of ischemic conditions of the heart or of a weakened myocardial contractile force, or for the prevention of sudden cardiac death. The benzamide I and/or its physiologically tolerable salts are preferably employed for this in the form of pharmaceutical preparations that are tailored with respect to their composition and the administration form to the medicinal effects desired in the specific case, for example in the form of solid preparations such as tablets or capsules or in the form of liquid preparations such as solutions for injections and infusions.

For the production of pharmaceutical preparations, it is often advantageous to employ a pharmaceutical active compound which contains an acidic group or a basic group in the form of a specific salt which has, for example, a more favorable solubility, a more favorable absorption behavior, a more favorable stability, or generally a more favorable property profile. The use of a specific salt, for example, can also have advantages in the preparation of the active compound or of the pharmaceutical preparations, or advantages with respect to adherence to the requirements of drug regulatory authorities. In particular for the production of solutions of pharmaceutical active compounds, especially of solutions which, as a solvent, contain only water or mainly water, it is often advantageous, for the obtainment of an adequate solubility, to employ a pharmaceutical active compound in the form of a suitable physiologically tolerable salt.

The hydrogen atom on that nitrogen atom of the thiourea group in the benzamide I which is bonded to the sulfonyl group has a relatively high acidity. The benzamide I can form salts with bases, for example metal salts, wherein a hydrogen atom is replaced by a monovalent metal ion or one equivalent of a polyvalent metal ion and which can be formally represented by formula II

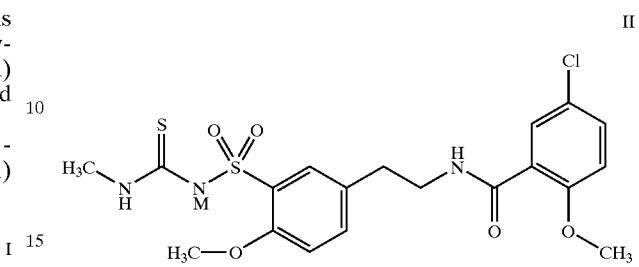

II wherein the cation M can be, for example, a monovalent metal cation or one equivalent of a polyvalent metal cation, for example a sodium ion, a potassium ion, or one equivalent of a calcium ion or magnesium ion. An advantageous salt for use in pharmaceutical preparations is the sodium salt of the benzamide I, which can be formally represented by formula III.

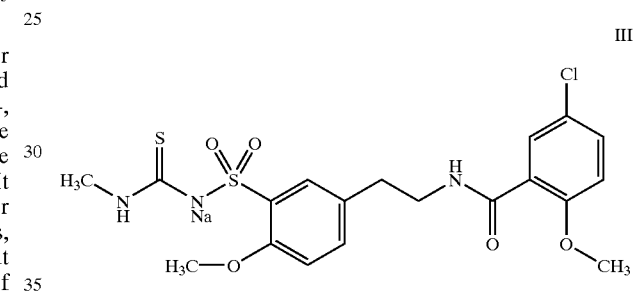

III

Formula III, however, is not to be understood as meaning that it shows, in each case for the solid or the dissolved sodium salt, the actual relative arrangement of the sodium ion and of the organic anion. The sodium ion can also be located in another position relative to the atoms in the anion; for example it can be coordinated to the sulfur atom of the thiourea group. The sodium salt of the benzamide I can, for example, likewise be represented by formula IV

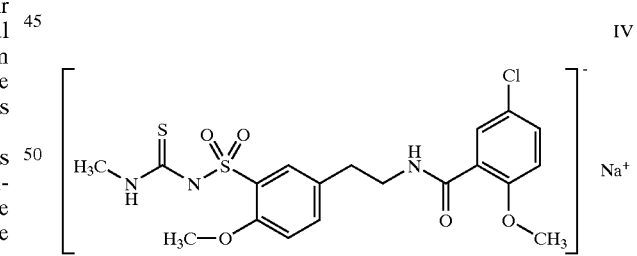

IV which, however, in turn is not to be understood as meaning that the single bonds and double bonds indicated therein represent the actual bonding conditions, or it can be represented by the empirical formula $C_9H_{21}ClN_3NaO_5S_2$.

The preparation of the benzamide I is carried out according to the details in U.S. Pat. Nos. 5,574,069 and 5,776,980 and corresponding publications, for example EP-A-612 724, by deprotonating 5-chloro-2-methoxy-N-(2-(4-methoxy-3-aminosulfonylphenyl)ethyl)benzamide in the aprotic solvent dimethylformamide using sodium hydride and then reacting it with methyl isothiocyanate. The isolation of the sodium salt of the benzamide I intermediately resulting here from the reaction mixture is not described, and the sodium salt is also not characterized in more detail. By pouring the reaction mixture into hydrochloric acid, the sodium salt is converted into the neutral sulfonylthiourea of formula I, which is isolated by filtration. The sodium salt itself can be isolated from the reaction mixture described in the prior art only with great difficulty. The salt remains clearly dissolved in the reaction mixture obtained. It is not possible to precipitate out a filterable solid by cooling or evaporation. On addition of nonpolar solvents such as, for example, diisopropyl ether, the reaction product precipitates in the form of an oil that is heavily contaminated and is unsuitable for use in pharmaceutical preparations and would only be usable after laborious purification operations. Moreover, in the process described in the prior art for the preparation of the sodium salt, sodium hydride is employed and hydrogen gas is released, which necessitates complicated precautions in terms of apparatus and safety measures for carrying out on a large industrial scale. It is an object of the present invention to make available, in a simple manner suitable for carrying out on a large industrial scale, the sodium salt of the benzamide I in a form suitable for pharmaceutical use.

It has now been found that the sodium salt of the benzamide I can be prepared in a solid crystalline form suitable for pharmaceutical use by reaction of the benzamide I with basic sodium compounds, for example sodium hydroxide or sodium alcoholates. Surprisingly, it turned out here that the solid crystalline sodium salt of the benzamide I can occur in a number of different crystal modifications, i.e., in polymorphic forms, which can be prepared specifically by adjustment of the reaction conditions and/or of the crystallization conditions and which differ in their physicochemical properties. Thus, these crystal modifications differ, for example, in their solubility, rate of dissolution, or behavior during pharmaceutical processing, and allow the production of pharmaceutical preparations having different property profiles starting from a single parent compound. The present invention thus relates to the crystalline sodium salt of 5-chloro-2-methoxy-N(2-(4-methoxy-3-methyl-aminothiocarbonylaminosulfonylphenyl)ethyl)benzamide and in particular to the individual polymorphic forms of the crystalline sodium salt of 5-chloro-2-methoxy-N-(2-(4-methoxy-3-methylaminothiocarbonylamino-sulfonylphenyl)ethyl)benzamide which are characterized, for example, by their physicochemical data indicated below. The invention relates in particular to:

crystal modification 1 (polymorphic form 1) of the sodium salt of 5-chloro-2-methoxy-N-(2-(4-methoxy-3-methylaminothiocarbonylaminosulfonylphenyl)ethyl) benzamide which has X-ray reflections at the following diffraction angles 2Theta (in°) in the X-ray diffraction diagram using Cu $K_{\alpha 1}$ radiation:
strong X-ray reflections: 8.95°;
medium-strong X-ray reflections: 7.10°, 11.35°, 12.15°, 15.40°, 22.80°, 23.00°, 23.50°;
crystal modification 2 (polymorphic form 2) of the sodium salt of 5-chloro-2-methoxy-N-(2-(4-methoxy-3-methylaminothiocarbonylaminosulfonylphenyl)ethyl) benzamide which has X-ray reflections at the following diffraction angles 2Theta (in°) in the X-ray diffraction diagram using Cu $K_{\alpha 1}$ radiation:
strong X-ray reflections: 7.15°, 11.10°, 22.85°, 23.10°, 26.80°;
medium-strong X-ray reflections: 9.90°, 13.35°, 13.80°, 14.00°, 14.90°, 18.95°, 19.85°, 21.60°, 22.55°, 23.90°, 24.30°, 25.45°, 27.15°, 28.25°, 28.35°, 28.95°;
crystal modification 3 (polymorphic form 3) of the sodium salt of 5-chloro-2-methoxy-N-(2-(4-methoxy-3-methylaminothiocarbonylaminosulfonylphenyl)ethyl) benzamide which has X-ray reflections at the following diffraction angles 2Theta (in°) in the X-ray diffraction diagram using Cu $K_{\alpha 1}$ radiation:
strong X-ray reflections: 8.35°, 11.75°, 11.95°, 13.70°, 19.75°, 20.90°, 21.90°, 24.90°, 26.40°, 28.45°;
medium-strong X-ray reflections: 12.45°, 15.80°, 16.45°, 18.10°, 18.45°, 19.35°, 19.45°, 21.40°, 22.20°, 23.00°, 25.15°, 25.45°, 30.15°;
crystal modification 4 (polymorphic form 4) of the sodium salt of 5-chloro-2-methoxy-N-(2-(4-methoxy-3-methylaminothiocarbonylaminosulfonylphenyl)ethyl) benzamide which has X-ray reflections at the following diffraction angles 2Theta (in°) in the X-ray diffraction diagram using Cu $K_{\alpha 1}$ radiation:
strong X-ray reflections: 8.70°, 8.95°, 10.85°, 12.20°, 20.50°, 21.30°, 23.85°; medium-strong X-ray reflections: 7.40°, 10.45°, 12.60°, 15.65°, 16.30°, 17.75°, 18.10°, 19.20°, 22.90°, 24.60°, 25.35°, 25.60°, 25.95°, 28.70°.

The indicated X-ray diffraction data were obtained from crystal powders in transmission on a STADIP two-circle diffractometer from Stoe (Darmstadt, Germany). The indicated diffraction angles 2Theta of the X-ray reflections are values rounded to a multiple of 0.050. X-ray reflections which have a rounded relative intensity of 50% or more of the intensity of the strongest reflection are designated here as strong X-ray reflections, and X-ray reflections which have a rounded relative intensity of 20% or more, but less than 50%, of the intensity of the strongest reflection are designated here as medium-strong X-ray reflections. Further details regarding the X-ray diffraction diagrams, which can also serve for further characterization of the crystal modifications 1, 2, 3, and 4, are found below. The X-ray diffraction diagrams obtained under the conditions indicated are shown in FIGS. 1 to 4 (FIG. 1 is the diffraction diagram of crystal modification 1, FIG. 2 that of crystal modification 2, FIG. 3 that of crystal modification 3, and FIG. 4 that of crystal modification 4). In the figures, the diffraction angle 2Theta (in°) is plotted in the abscissa direction and the intensity is plotted in the ordinate direction.

The crystal modifications 1, 2, 3, and 4 of the sodium salt of the benzamide I are well-crystalline colorless solids, which are excellently filterable, can be dried rapidly, and are even pourable in the dry state. The solids are stable on storage at the customary temperatures and also at medium to higher atmospheric humidities. Depending on the crystal modification, they have an excellent water solubility on account of which they are particularly advantageously suitable for use in pharmaceutical preparations, in particular for the production of solutions which are intended, for example, for intravenous administration, but also for the production of pharmaceutical forms to be administered orally. On account of their high crystallizability, the crystal modifications according to the invention are obtainable by simple means in a high purity which allows pharmaceutical use without additional purification steps, and which thus essentially simplifies the production process for the preparation of the active compound on a large industrial scale and reduces the cost due to the saving of time, apparatus, and solvents. The invention comprises the crystalline sodium salt of the benzamide I and in particular its crystal modifications 1, 2, 3, and 4 both in solvent-free from and in the form of solvates, for example hydrates or adducts with alcohols such as methanol or ethanol.

The present invention furthermore relates to processes for the preparation of the sodium salt of the benzamide I, in particular processes according to which the crystalline sodium salt and especially the crystal modifications 1, 2, 3, and 4 described above are obtainable. The sodium salt of 5-chloro-2-methoxy-N-(2-(4-methoxy-3-methyl-aminothiocarbonylaminosulfonylphenyl)ethyl)benzamide can generally be prepared by a process comprising reacting 5-chloro-2-methoxy-N-(2-(4-methoxy-3-methyl-aminothiocarbonylaminosulfonylphenyl)ethyl)benzamide with a basic sodium compound in the presence of a solvent (or diluent) or solvent mixture. By adjusting the process parameters the salts can be obtained in the desired crystalline form. The technical implementation of the reaction and isolation of the product can be carried out by the customary standard procedures familiar to the person skilled in the art.

Suitable basic sodium compounds for converting the benzamide I into the sodium salt are, for example, sodium hydroxide and sodium alcoholates, in particular the sodium salts of $(C_1–C_4)$-alkanols such as sodium methoxide (=sodium methylate), sodium ethoxide (=sodium ethylate), or sodium propoxide (=sodium propylate), but also, for example, sodium compounds such as sodium carbonate or sodium hydrogencarbonate. Preferred basic sodium compounds are sodium hydroxide, sodium methoxide, and sodium ethoxide, in particular sodium hydroxide. In the conversion of the benzamide I into the salt two or more basic sodium compounds also can be present, for example sodium hydroxide together with one or both of the compounds sodium methoxide and sodium ethoxide. Sodium compounds such as sodium hydroxide or sodium alcoholates are preferably employed in equimolar amount or in an excess, based on the benzamide I. Preferably, about 1 to about 2 mol, more preferably about 1 to about 1.5 mol, and even more preferably about 1 to about 1.3 mol, of sodium hydroxide and/or sodium alcoholate are employed per mole of benzamide I. The basic sodium compounds can be employed in solid form or in the form of solutions or suspensions.

Preferred solvents for the conversion of the benzamide I into the sodium salt are polar organic solvents, for example alcohols, in particular $(C_1–C_4)$-alkanols such as methanol, ethanol, n-propanol, or isopropanol, ethers such as tetrahydrofuran, dioxane, or mono- and dimethyl and mono- and diethyl ethers of ethylene glycol and diethylene glycol, amides such as dimethylformamide or N-methylpyrrolidone, and others, for example dimethyl sulfoxide. There can also be employed mixtures of two or more solvents, in particular mixtures of two or more of the abovementioned solvents, for example mixtures of two alcohols, such as mixtures of methanol and ethanol or mixtures of one or more alcohols with one or more ethers. Furthermore, both the individual solvents and the mixtures of two or more solvents can also be employed in the presence of water or as a mixture with water. The mixtures of two or more organic solvents or of organic solvents and water can contain the components in any desired quantitative ratios, the quantitative ratios preferably being selected such that a single-phase solvent mixture is present. Preferred solvents are methanol, ethanol, mixtures of methanol and ethanol, mixtures of methanol and water, mixtures of ethanol and water, and mixtures of methanol, ethanol, and water. The amount of the solvent or solvent mixture can be chosen such that the starting compounds, i.e., the benzamide I and the basic sodium compound, are dissolved, but the amount can also be selected such that one or both starting compounds are only partially dissolved and a suspension is present. Even if a suspension is present, the sodium salt of the benzamide I is surprisingly obtained quantitatively and in high purity.

The reaction of the benzamide I with the basic sodium compound can be carried out in a wide temperature range. It is preferably carried out at temperatures from about −10° C. to about +100° C., when working under atmospheric pressure in particular at temperatures from about −10° C. to the boiling point of the solvent or solvent mixture used. It is particularly preferably carried out at temperatures from about −10° C. to about +50° C., more preferably from about 0° C. to about +35° C., in particular from about +5° C. to about +35° C. Frequently, it is favorable in the preparation of the sodium salts according to the invention to establish a number of temperatures or temperature ranges in succession, for example initially to bring the benzamide I into solution by heating to a higher temperature, then to lower the temperature and to add the basic sodium compound and later to lower the temperature still further for the isolation of the sodium salt. The salt formation can likewise be carried out in a wide pressure range, for example at pressures from about 0 bar to about 10 bar. It can be carried out under atmospheric pressure, that is at about 1 bar ($10^5$ Pa), but it can also be carried out under lower pressure, for example in a vacuum with removal of solvent by distillation, or under higher pressure, for example if it is intended to heat to temperatures above the boiling point of the solvent. Preferably, it is carried out at a pressure from about 1 bar to about 5 bar, in particular about 1 bar to about 2.5 bar.

The conversion of the benzamide I into its sodium salt can be carried out in customary equipment. On the larger scale, it is preferably carried out in a batch operation in customary stirring vessels, for example in glass or enameled vessels or stainless steel vessels. The benzamide I can be introduced initially and the basic sodium compound then added, or the basic sodium compound can be introduced initially and the benzamide I then added, or both starting compounds can also be metered simultaneously into the reaction vessel. The addition of a substance can be carried out in one or more portions or it can be metered in continuously. The actual reaction of the benzamide I with the basic sodium compound is in general completely terminated after a short time. In particular in the case of batches on a relatively large scale, the mixture is advantageously stirred under defined conditions for some time before the isolation of the sodium salt, for example about 1 to about 30 hours.

The work-up is preferably done by isolating the resulting solid crystalline sodium salt of the benzamide I by filtration or centrifugation. The sodium salt can be isolated from that solvent or solvent mixture in which the reaction of the benzamide I with the basic sodium compound was carried out, and at that temperature at which this reaction was carried out. Depending on the conditions under which the reaction is carried out, it can, however, also be advantageous in order to obtain a high yield and purity to first cool the mixture, before the isolation of the sodium salt, to a relatively low temperature, for example to room temperature or about 0° C., and/or to remove a part of the solvent by distillation at atmospheric pressure or in vacuum, and/or to add one or more further solvents, for example an alcohol or an ether in which the sodium salt is relatively poorly soluble. The isolated sodium salt can then be washed and dried as usual and, if desired, be purified still further, for example, by recrystallization.

The present invention relates in particular to processes for the preparation of the sodium salt of the benzamide I from the benzamide I and a basic sodium salt, in which by means of the defined adjustment of one or more reaction parameters, for example by means of the choice of the solvent and/or the temperature at which the reaction of the benzamide I with the basic sodium compound and/or the crystallization of the sodium salt are carried out, the crystal modifications 1, 2, 3, or 4 of the sodium salt described above are specifically obtained. If not specified otherwise, the above illustrations for carrying out the salt formation otherwise correspondingly apply to these processes described below.

The invention thus relates to a process for the preparation of crystal modification 1 of the sodium salt of 5-chloro-2-methoxy-N-(2-(4-methoxy-3-methylaminothiocarbonyl-aminosulfonylphenyl)ethyl)benzamide, comprising reacting 5-chloro-2-methoxy-N-(2-(4-methoxy-3-methylamino-thiocarbonylaminosulfonylphenyl)ethyl)benzamide with a basic sodium compound in a mixture of methanol and ethanol or a mixture of methanol, ethanol, and water and working at temperatures from about −10° C. to about +40° C. Preferably, this process is carried out at temperatures from about 0° C. to about +35° C., particularly preferably from about +20° C. to about +30° C. The basic sodium compound employed for the conversion of the benzamide I into the sodium salt is preferably sodium hydroxide. The proportions of the individual solvents which are contained in the solution or suspension of the one starting substance, and which are contained in the solution or suspension of the second starting substance, are variable. If the reaction is carried out in a mixture of methanol and ethanol, the methanol and ethanol are on the whole preferably employed in a ratio of about 0.5 to about 2 parts by volume of ethanol to 1 part by volume of methanol, particularly preferably about 0.8 to about 1.2 parts by volume of ethanol to 1 part by volume of methanol, for example about 1 part by volume of ethanol to 1 part by volume of methanol, for the preparation of the solvent mixture in which the reaction of the benzamide I with the basic sodium compound is carried out. The amount of water that can be present in addition to the methanol and ethanol in the solvent mixture employed is also variable. If the process is carried out in a mixture of methanol, ethanol, and water, on the whole the water is preferably employed in a volume which is to the sum of the volumes of the methanol and ethanol as about 0.001 to about 0.1 parts by volume of water to 1 part by volume of methanol plus ethanol, particularly preferably as about 0.005 to about 0.05 parts by volume of water to 1 part by volume of methanol plus ethanol, for example about 0.01 parts by volume of water to 1 part by volume of methanol plus ethanol, for the preparation of the solvent mixture in which the reaction of the benzamide I with the basic sodium compound is carried out. For this process and all other processes described, it applies that the parts by volume indicated for mixtures of solvents indicate the relative amounts of the pure solvents that are employed altogether when carrying out the reaction. The indicated parts by volume do not relate to the relative volumes in the mixture obtained which can be different as a result of the occurrence of mixing effects.

The present invention also relates to crystal modification 1 of the sodium salt of 5-chloro-2-methoxy-N-(2-(4-methoxy-3-methylaminothiocarbonylaminosulfonyl-phenyl)-ethyl)benzamide, which is obtainable by the process for the preparation of this crystal modification described above, in particular by the procedure and under the reaction conditions, for example with respect to the temperatures or the quantitative ratios, which are indicated in Example 3 described below.

The invention further relates to a process for the preparation of crystal modification 2 of the sodium salt of 5-chloro-2-methoxy-N-(2-(4-methoxy-3-methyl-aminothiocarbonylaminosulfonylphenyl)ethyl)benzamide, comprising reacting 5-chloro-2-methoxy-N-(2-(4-methoxy-3-methylaminothiocarbonylaminosulfonylphenyl)ethyl) benzamide with a basic sodium compound in methanol or a mixture of methanol and water and heating the mixture to a temperature of about +40° C. or higher, for example to a temperature from about +40° C. to about +80° C. Preferably, the mixture is heated in this process to a temperature from about +40° C. to about +70° C., particularly preferably to a temperature from about +50° C. to about +70° C. The time of heating depends on the procedure chosen in the individual case and is in general about 4 to about 30 hours, preferably about 4 to about 20 hours. If desired, it can be determined by analysis of the sodium salt that is isolated from a sample taken whether the formation of crystal modification 2 is already complete. As generally illustrated above for the preparation of the sodium salts of the benzamide I, it can be advantageous when carrying out this process as well as the other processes described to set a number of different temperatures successively. For example, in this process for the preparation of crystal modification 2 the benzamide I and the basic sodium compound can first be mixed together at a relatively low temperature, for example at room temperature or at a temperature from about +20° C. to about +30° C., then the mixture can be heated as indicated, and finally a lower temperature can be set again before the isolation of the sodium salt, for example a temperature from about 0° C. to about +10° C. The basic sodium compound employed for the conversion of the benzamide I into the sodium salt is preferably sodium hydroxide. If the reaction is carried out in a mixture of methanol and water, the proportions of the individual solvents which are contained in the solution or suspension of the one starting substance, and which are contained in the solution or suspension of the second starting substance, are variable. If the reaction is carried out in a mixture of methanol and water, on the whole the methanol and water are preferably employed in a ratio of about 0.001 to about 0.1 parts by volume of water to 1 part by volume of methanol, particularly preferably in a ratio of about 0.005 to about 0.05 parts by volume of water to 1 part by volume of methanol, for example about 0.02 parts by volume of water to 1 part by volume of methanol, for the preparation of the solvent mixture in which the reaction of the benzamide I with the basic sodium compound is carried out.

The present invention also relates to crystal modification 2 of the sodium salt of 5-chloro-2-methoxy-N-(2-(4-methoxy-3-methylaminothiocarbonylaminosulfonyl-phenyl)-ethyl)benzamide, which is obtainable by the process described above for the preparation of this crystal modification, in particular by the procedure and under the reaction conditions, for example with respect to the temperatures or the quantitative ratios, which are indicated in Example 7 described below.

The invention further relates to a process for the preparation of crystal modification 3 of the sodium salt of 5-chloro-2-methoxy-N-(2-(4-methoxy-3-methyl-aminothiocarbonylaminosulfonylphenyl)ethyl)benzamide, comprising reacting 5-chloro-2-methoxy-N-(2-(4-methoxy-3-methylaminothiocarbonylaminosulfonylphenyl)ethyl) benzamide with a basic sodium compound in methanol, in a mixture of methanol and water, in tetrahydrofuran, in dimethylformamide, in N-methylpyrrolidone, or in dimethyl sulfoxide, or in a mixture of methanol and one or more of the solvents tetrahydrofuran, dimethylformamide, N-methylpyrrolidone, and dimethyl sulfoxide, and working at temperatures from about −10° C. to about +40° C. Preferably, this process is carried out at temperatures from about 0° C. to about +35° C., particularly preferably from about +20° C. to about +30° C. The basic sodium compound employed for the conversion of the benzamide I into the sodium salt is preferably sodium hydroxide or a sodium ($C_1$–$C_4$)-alkoxide, particularly preferably sodium hydroxide, sodium methoxide, or sodium ethoxide, in particular sodium hydroxide. Preferred solvents are methanol and a mixture of methanol and water, in particular methanol.

If the reaction is carried out in a mixture of solvents, for example of methanol and water, of methanol and N-methylpyrrolidone, of methanol and tetrahydrofuran, or of methanol and dimethyl sulfoxide, the proportions of the individual solvents which are contained in the solution or suspension of the one starting substance, and which are contained in the solution or suspension of the second starting substance, are variable. If the reaction is carried out in a mixture of methanol and water, on the whole the methanol and water are preferably employed in a ratio of about 0.001 to about 0.1 parts by volume of water to 1 part by volume of methanol, particularly preferably about 0.005 to about 0.05 parts by volume of water to 1 part by volume of methanol, for example about 0.02 parts by volume of water to 1 part by volume of methanol, for the preparation of the solvent mixture in which the reaction of the benzamide I with the basic sodium compound is carried out. If the reaction is carried out in a mixture of methanol and N-methylpyrrolidone, on the whole the methanol and N-methylpyrrolidone are preferably employed in a ratio of about 0.05 to about 1 part by volume of N-methylpyrrolidone to 1 part by volume of methanol, particularly preferably about 0.1 to about 0.5 parts by volume of N-methylpyrrolidone to 1 part by volume of methanol, for example about 0.4 parts by volume of N-methylpyrrolidone to 1 part by volume of methanol, for the preparation of the solvent mixture in which the reaction of the benzamide I with the basic sodium compound is carried out. If the reaction is carried out in a mixture of methanol and tetrahydrofuran, on the whole the methanol and tetrahydrofuran are preferably employed in a ratio of about 5 to about 40 parts by volume of tetrahydrofuran to 1 part by volume of methanol, particularly preferably about 10 to about 30 parts by volume of tetrahydrofuran to 1 part by volume of methanol, for example about 20 parts by volume of tetrahydrofuran to 1 part by volume of methanol, for the reaction of the solvent mixture in which the reaction of the benzamide I with the basic sodium compound is carried out.

As generally illustrated above for the preparation of the sodium salt of the benzamide I, it can be advantageous when carrying out this process as well as the other processes described to additionally add one or more further solvents to the mixture for the isolation of the sodium salt. For example, in this process for the preparation of crystal modification 3 a solvent such as ethanol, isopropanol, or diisopropyl ether can be added to the mixture, or the mixture can be metered into a solvent such as, for example, ethanol, the amount of ethanol, isopropanol, or diisopropyl ether being variable. If the reaction of the benzamide I with the basic sodium compound is carried out in methanol or a mixture of methanol and water and a further solvent is to be added for the isolation of the sodium salt, ethanol is preferably used. In an isolation of the sodium salt of this type from a mixture of methanol and ethanol or methanol, water, and ethanol, the ethanol is preferably employed in a ratio of about 0.5 to about 10 parts by volume of ethanol to 1 part by volume of methanol, particularly preferably in a ratio of about 1 to about 5 parts by volume of ethanol to 1 part by volume of methanol. Preferably, in this process for the preparation of crystal modification 3 the isolation of the product is carried out without adding a further solvent.

The present invention also relates to crystal modification 3 of the sodium salt of 5-chloro-2-methoxy-N-(2-(4-methoxy-3-methylaminothiocarbonylaminosulfonyl-phenyl)-ethyl)benzamide, which is obtainable by the process for the preparation of this crystal modification described above, in particular by the procedure and under the reaction conditions, for example with respect to the temperatures, the solvents, and the quantitative ratios, which are indicated in Examples 1, 2, 4, 5, and 11 described below.

The invention further relates to a process for the preparation of crystal modification 4 of the sodium salt of 5-chloro-2-methoxy-N-(2-(4-methoxy-3-methyl-aminothiocarbonylaminosulfonylphenyl)ethyl)benzamide, comprising reacting 5-chloro-2-methoxy-N-(2-(4-methoxy-3-methylaminothiocarbonylaminosulfonyl-phenyl)ethyl)benzamide with a basic sodium compound in ethanol or a mixture of ethanol and water and working at temperatures from about −10° C. to about +40° C. Preferably, this process is carried out at temperatures from about 0° C. to about +35° C., particularly preferably from about +20° C. to about +30° C. The basic sodium compound employed for the conversion of the benzamide I into the sodium salt is preferably sodium hydroxide. If the reaction is carried out in a mixture of ethanol and water, the proportions of the individual solvents which are contained in the solution or suspension of the one starting substance, and which are contained in the solution or suspension of the second starting substance, are variable. If the reaction is carried out in a mixture of ethanol and water, on the whole the ethanol and water are preferably employed in a ratio of about 0.001 to about 0.1 parts by volume of water to 1 part by volume of ethanol, particularly preferably about 0.005 to about 0.05 parts by volume of water to 1 part by volume of ethanol, for example about 0.02 parts by volume of water to 1 part by volume of ethanol, for the preparation of the solvent mixture in which the reaction of the benzamide I with the basic sodium compound is carried out.

The present invention also relates to crystal modification 4 of the sodium salt of 5-chloro-2-methoxy-N-(2-(4-methoxy-3-methylaminothiocarbonylaminosulfonyl-phenyl)-ethyl)benzamide, which is obtainable by the process described above for the preparation of this crystal modification, in particular by the procedure and under the reaction conditions, for example with respect to the temperatures or the quantitative ratios, which are indicated in Example 6 described below.

The invention furthermore relates to processes by which the various crystal modifications of the sodium salt of the benzamide I can be converted into one another, for example by converting one crystal modification into another crystal modification in a certain solvent or solvent mixture by adjusting a certain temperature, if appropriate with addition of auxiliaries such as, for example, a dispersant or of seed crystals of the crystal modification to be produced. For these processes described below, the above illustrations for the procedure of the preparation of the sodium salt of the benzamide I from the benzamide I correspondingly apply. For example, the conversion of one crystal modification into another crystal modification can also be carried out at atmospheric pressure or can be carried out under elevated pressure in a pressure-resistant reactor, for example at pressures of about 1 bar to about 5 bar, or the isolation of the product can be carried out by filtration or centrifugation, if desired after removal of a part of the solvent by distillation and/or with addition of one or more further solvents and/or after cooling.

The invention thus relates to a process for the preparation of crystal modification 2 of the sodium salt of 5-chloro-2-methoxy-N-(2-(4-methoxy-3-methylaminothiocarbonyl-aminosulfonylphenyl)ethyl)benzamide, comprising heating crystal modification 1 or crystal modification 3 of the sodium salt of 5-chloro-2-methoxy-N-(2-(4-methoxy-3-methylaminothiocarbonylaminosulfonylphenyl)ethyl) benzamide to a temperature of about +40° C. or higher, for example to a temperature from about +40° C. to about +80° C., in methanol or a mixture of methanol and water. The conversion is preferably carried out in methanol. The conversion is preferably carried out by heating to a temperature from about +40° C. to about +70° C., particularly preferably to a temperature from about +50° C. to about +70° C. The time of heating depends on the procedure chosen in the individual case. In general, for complete conversion heating is carried out for about 4 to about 30 hours, preferably about 4 to about 20 hours, particularly preferably about 5 to about 10 hours. If desired, it can be determined by analysis of the sodium salt that is isolated from a sample taken whether the conversion into crystal modification 2 is already complete. If the reaction is carried out in a mixture of methanol and water, the proportions of the individual solvents are variable. If the reaction is carried out in a mixture of methanol and water, the water is preferably employed in a ratio of about 10.001 to about 0.1 parts by volume of water to 1 part by volume of methanol, particularly preferably in a ratio of about 0.005 to about 0.05 parts by volume of water to 1 part by volume of methanol.

The present invention also relates to crystal modification 2 of the sodium salt of 5-chloro-2-methoxy-N-(2-(4-methoxy-3-methylaminothiocarbonyl-aminosulfonyl-phenyl)-ethyl)benzamide, which is obtainable from crystal modification 1 or crystal modification 3 by the process described above, in particular under the reaction conditions, for example with respect to the temperatures or quantitative ratios, which are indicated in Examples 8 and 9 described below.

The invention also relates to a process for the preparation of crystal modification 3 of the sodium salt of 5-chloro-2-methoxy-N-(2-(4-methoxy-3-methylaminothiocarbonyl-aminosulfonylphenyl)ethyl)benzamide, comprising heating crystal modification 4 of the sodium salt of 5-chloro-2-methoxy-N-(2-(4-methoxy-3-methylaminothiocarbonyl-aminosulfonylphenyl)ethyl)benzamide to a temperature of about +75° C. or higher, for example to a temperature from about +75° C. to about +100° C., in ethanol or a mixture of ethanol and water. The conversion is preferably carried out in ethanol. The conversion is preferably carried out by heating to a temperature from about +75° C. to about +95° C., particularly preferably to a temperature from about +85° C. to about +95° C., in particular to a temperature from about +85° C. to about +90° C. The time of heating depends on the procedure chosen in the individual case. In general, for complete conversion heating is carried out for about 4 to about 30 hours, preferably about 6 to about 20 hours. If desired, it can be determined by analysis of the sodium salt that is isolated from a sample taken whether the conversion into crystal modification 3 is already complete. If the reaction is carried out in a mixture of ethanol and water, the proportions of the individual solvents are variable. If the reaction is carried out in a mixture of ethanol and water, the water is preferably employed in a ratio of about 0.001 to about 0.1 parts by volume of water to 1 part by volume of ethanol, particularly preferably in a ratio of about 0.005 to about 0.05 parts by volume of water to 1 part by volume of ethanol.

The present invention also relates to crystal modification 3 of the sodium salt of 5-chloro-2-methoxy-N-(2-(4-methoxy-3-methylaminothiocarbonylaminosulfonyl-phenyl)-ethyl)benzamide, which is obtainable from crystal modification 4 by the process described above, in particular under the reaction conditions, for example with respect to the temperatures or the quantitative ratios, which are indicated in Example 10 described below.

The conversion of one crystal modification into another crystal modification can also be carried out in situ, i.e., the sodium salt of the benzamide I can first be produced in a certain crystal modification from the benzamide I and a basic sodium compound by one of the processes described above and this crystal modification can then be converted into another crystal modification without isolation by one of the conversion processes described.

The benzamide I, which is needed as a starting material for the process described above for the preparation of its sodium salt by reaction with a basic sodium compound, can be prepared starting from commercially available compounds, for example by the processes which are described in U.S. Pat. Nos. 5,574,069 and 5,776,980 and corresponding publications, for example EP-A-612 724. According to these processes, for example, 2-(4-methoxyphenyl)ethylamine is first acylated in pyridine with 5-chloro-2-methoxybenzoyl chloride to give 5-chloro-2-methoxy-N-(2-(4-methoxyphenyl)ethyl)benzamide. This compound is converted into 5-chloro-2-methoxy-N-(2-(4-methoxy-3-chlorosulfonylphenyl)ethyl)benzamide by introduction into cold chlorosulfonic acid. The sulfonyl chloride is converted into 5-chloro-2-methoxy-N-(2-(4-methoxy-3-aminosulfonylphenyl)ethyl)benzamide with ammonia in water/acetone. The sulfonamide is reacted first with sodium hydride and then with methyl isothiocyanate in dimethylformamide as already explained, and the reaction mixture is worked up by introduction into aqueous hydrochloric acid. With respect to the particulars, reference is made to the details in U.S. Pat. Nos. 5,574,069 and 5,776,980 and corresponding publications, for example EP-A-612 724, which are incorporated herein by reference and the respective contents of which are part of the present disclosure. The benzamide I, which is employed in the preparation of the forms of the sodium salt according to the invention, can be employed directly in the form in which it is obtained in its preparation, or it can first be washed, for example, with a solvent and/or be dried or be treated in another manner. Advantageously, drying of the benzamide I can be dispensed with and it can be employed in moist form for the preparation of the sodium salt, in particular if the solvent still contained is the same in which the preparation of the sodium salt according to the invention takes place.

The pharmacological properties of the crystalline sodium salt of 5-chloro-2-methoxy-N-(2-(4-methoxy-3-methylaminothiocarbonylaminosulfonylphenyl)ethyl) benzamide and crystal modifications 1, 2, 3, and 4 and their possible uses for the therapy and prophylaxis of disorders are, if the substances are present in the target organ or in the target cell in dissolved form, independent of the original form of the solid and thus correspond to those which are described in U.S. Pat. Nos. 5,574,069 and 5,776,980 and corresponding publications, for example EP-A-612 724. Like the benzamide I and its physiologically tolerable salts in general, its sodium salt in crystal modifications 1, 2, 3, and 4 blocks ATP-sensitive potassium channels in heart muscle cells in ATP deficiency conditions, such as occur in the heart muscle cell in ischemias (ATP=adenosine triphosphate). The opening of ATP-sensitive potassium channels caused by the lowering of the ATP level leads to a shortening of the action potential duration and counts as one of the causes of so-called reentry arrhythmia, which can lead to sudden cardiac death. By means of the use of the crystal modifications of the sodium salt of the benzamide I according to the invention, this harmful opening of the potassium channels can be prevented. The action of crystal modifications 1, 2, 3, and 4 can be investigated, for example, in the pharmacological models which are described in U.S. Pat. Nos. 5,574,069 and 5,776,980 and corresponding publications, for example EP-A-612 724, which are incorporated herein by reference and the respective contents of which are part of the present disclosure.

The crystal modifications of the sodium salt of the benzamide I according to the invention with their antifibrillatory action are therefore valuable pharmaceuticals for the treatment and prevention of cardiac arrhythmia of very different origin, and can be used as antiarrhythmics and in particular for the prevention of sudden cardiac death due to arrhythmia. Examples of arrhythmic disorders of the heart are supraventricular arrhythmias, for example atrial tachycardia, atrial flutter, or paroxysmal supraventricular arrhythmias, or ventricular arrhythmias, such as ventricular extrasystoles, but in particular life-threatening ventricular tachycardia and the particularly dangerous ventricular fibrillation. They are particularly suitable for those cases in which arrhythmias are a result of a constriction of a coronary vessel, such as occur, for example, in angina pectoris or during an acute cardiac infarct or as a chronic result of a cardiac infarct. They are therefore generally suitable for use in ischemic conditions of the heart and are particularly suitable in postinfarct patients for the prevention of sudden cardiac death. Further syndromes in which arrhythmias of this type and/or sudden cardiac death due to arrhythmia play a role are cardiac insufficiency or cardiac hypertrophy as a result of chronically raised blood pressure.

Moreover, the crystal modifications of the sodium salt of the benzamide I according to the invention can positively influence a decreased contractility of the heart. In this context, a gradual disease-related decline in cardiac contractility can be of concern, for example in cardiac insufficiency, but also acute cases such as heart failure in the case of the effects of shock. Likewise, by administration of the crystal modifications of the sodium salt of the benzamide I according to the invention during a heart transplant, the heart can resume its functional capacity more rapidly and more reliably after operation has taken place. The same applies to operations on the heart which make necessary a temporary stoppage of heart activity by cardioplegic solutions. The crystal modifications of the sodium salt of the benzamide I according to the invention can also be used for the protection of the organs in the donor before and during removal, for the protection of removed organs, for example, during treatment or on storage in physiological bath fluids, and during transfer to the recipient's body. The crystal modifications according to the invention can furthermore be used for the treatment and prophylaxis of vagal dysfunctions.

The crystal modifications of the sodium salt of the benzamide I according to the invention can thus be used in animals, preferably in mammals, and in particular in humans as pharmaceuticals on their own, in mixtures with one another, or in the form of pharmaceutical preparations (or pharmaceutical compositions). The present invention therefore also relates to the crystalline sodium salt of the benzamide I and the crystal modifications of the sodium salt of the benzamide I according to the invention for use as pharmaceuticals, their use for inhibiting ATP-sensitive potassium channels, and in particular their use in the therapy and prophylaxis of the abovementioned syndromes, and also their use for the production of medicaments therefor. The present invention furthermore relates to pharmaceutical preparations which contain, as active constituents, an efficacious dose of the crystalline sodium salt of the benzamide I, in particular of the sodium salt of the benzamide I in the form of one or more of the crystal modifications 1, 2, 3, and 4 according to the invention, and a pharmaceutically tolerable carrier, that is one or more vehicles and/or excipients. These pharmaceutical preparations contain, for example, the sodium salt of the benzamide I in crystal modification 1 and a pharmaceutically tolerable carrier, or the sodium salt of the benzamide I in crystal modification 2 and a pharmaceutically tolerable carrier, or the sodium salt of the benzamide I in crystal modification 3 and a pharmaceutically tolerable carrier, or the sodium salt of the benzamide I in crystal modification 4 and a pharmaceutically tolerable carrier, or, for example, two of the crystal modifications according to the invention such as modifications 1 and 2, or modifications 1 and 3, or modifications 1 and 4, or modifications 2 and 3, or modifications 2 and 4, or modifications 3 and 4, in each case together with a pharmaceutically tolerable carrier.

The pharmaceutical preparations normally contain, for example, about 0.2 to about 800 mg, preferably about 1 to about 400 mg, of the crystal modifications of the sodium salt of the benzamide I according to the invention and one or more pharmaceutically innocuous vehicles and/or excipients (or additives or auxiliaries) and, if desired, one or more other active compounds. However, depending on the nature of the pharmaceutical preparation, the amount of sodium salt of the benzamide I contained can also be larger. The pharmaceutical preparations can be produced in a manner known per se. For this, one or more crystal modifications of the sodium salt of the benzamide I according to the invention are brought into a suitable administration and dosage form together with one or more solid or liquid pharmaceutical vehicles and/or excipients, and, if the preparation of a combination preparation is desired, one or more other pharmaceutical active compounds having therapeutic or prophylactic action, which can then be used as pharmaceuticals in human medicine or veterinary medicine. In the preparation of liquid pharmaceutical forms, in particular, for example, of solutions for intravenous administration, a freeze-drying step can advantageously also be carried out. For this, the sodium salt of the benzamide I is dissolved, the good water solubility and high dissolution rate being of particular advantage, and after sterile filtration the solution is freeze-dried. The freeze-drying product obtained and appropriately packed is then dissolved again before administration, for example in water. The pharmaceutical preparations normally contain about 0.5 to about 90 percent by weight of the crystal modifications of the sodium salt of the benzamide I according to the invention, but depending on the nature of the preparation the content can also be, for example, higher. Possible other pharmaceutical active compounds are, for example, other substances having cardiovascular activity such as, for example, calcium antagonists, NO donors, or ACE inhibitors. If desired, for example, one or more vitamins can also be contained as further active compounds.

Suitable vehicles for the pharmaceutical preparations are organic and/or inorganic substances which are suitable, for example, for enteral (for example oral) administration, parenteral (for example intravenous, intramuscular, or subcutaneous) administration, topical or percutaneous application, or for other administration forms, for example for implants, and do not react with the sodium salt of the benzamide I in an undesired manner, for example water, physiological saline solution, vegetable oils, benzyl alcohols, polyethylene glycols, glycerol triacetate, gelatin, carbohydrates such as lactose or starch, magnesium stearate, talc, lanolin, or petroleum jelly. For parenteral administration, for example by injection or infusion, preferably solutions, particularly preferably aqueous solutions, are used. For oral or rectal administration preferably solutions, particularly preferably aqueous or oily solutions, suspensions, emulsions, tablets, coated tablets, capsules, syrups, juices, drops, or suppositories are used. For topical administration preferably ointments, creams, pastes, lotions, gels, sprays, foams, aerosols, powders, or solutions, for example solutions in water or alcohols such as ethanol, isopropanol, or 1,2-propanediol or mixtures thereof with one another or with water, are used. In particular for topical application, liposomal preparations are also suitable. The pharmaceutical preparations can furthermore contain, for example, excipients such as stabilizers, wetting agents, emulsifiers, salts, lubricants, preservatives, agents for influencing the osmotic pressure, agents for achieving a depot effect, buffer substances, colorants, flavorings, and/or aromatizers.

The dose of the crystal modifications of the sodium salt of the benzamide I according to the invention, which is to be administered, for example, for the treatment of cardiac arrhythmias or for the prevention of sudden cardiac death, is to be tailored to the individual conditions as customary for an optimal action. It thus depends on the nature and severity of the disease to be treated, the sex, age, weight, and the individual responsiveness of the person or animal to be treated, the modification, the administration form, on whether treatment is acute or chronic or prophylaxis is carried out, or on whether further active compounds are administered in addition to the crystal modifications of the sodium salt of the benzamide I according to the invention. Normally, a dose is applied which is at least about 0.01 mg, preferably at least about 0.1 mg, in particular at least about 1 mg, and which is at most about 100 mg, preferably at most about 10 mg, in particular if prophylaxis is carried out (all above mg data are mg of crystal modification according to the invention per kg of body weight and per day on administration to an adult weighing about 75 kg). The dose can be administered as an individual dose or divided into a number, for example 2, 3, or 4, individual doses. In particular when acute cases of cardiac arrhythmia are treated, for example in an intensive care unit, parenteral administration can be advantageous. A preferred dose in critical situations can then be about 10 mg to about 100 mg per kg of body weight and day and can be administered, for example, as an intravenous continuous infusion. If appropriate, it may be necessary, depending on individual behavior, to deviate upwards or downwards from the doses indicated.

On account of their inhibitory action on ATP-sensitive potassium channels, the crystal modifications of the sodium salt of the benzamide I according to the invention can also be employed, apart from as pharmaceutical active compounds in human and veterinary medicine, as a scientific tool or as an aid in research, for example in biochemical investigations in which an influence on potassium channels of this type is intended, and also for diagnostic purposes, for example in the in vitro diagnosis of cell samples or tissue samples. The crystal modifications of the sodium salt of the benzamide I according to the invention can also be used as intermediates for the production of further pharmaceutical active compounds.

The following examples illustrate the invention.

EXAMPLE 1

40 kg of 5-chloro-2-methoxy-N-(2-(4-methoxy-3-methylaminothiocarbonylaminosulfonylphenyl)ethyl)benzamide were suspended in 80 l of methanol in an enameled stirring vessel and the temperature was adjusted to 27° C. A solution of 4.7 kg of sodium hydroxide in 58 l of methanol and 3.2 l of water was then metered in in the course of 10 to 15 minutes. The mixture was stirred at 27° C. for 3 hours (h). 136 l of ethanol were then added with stirring. The mixture was then stirred for 1 h at 20° C. to 25° C. The precipitated product was filtered off and washed with ethanol. After drying, 38.2 kg of the sodium salt of 5-chloro-2-methoxy-N-(2-(4-methoxy-3-methylaminothiocarbonylaminosulfonylphenyl)ethyl)benzamide in crystal modification 3 were obtained.

EXAMPLE 2

4.4 kg of sodium hydroxide were completely dissolved in 160 l of methanol at 20° C. to 23° C. in a stirring vessel. 51 kg of 5-chloro-2-methoxy-N-(2-(4-methoxy-3-methylaminothiocarbonylaminosulfonylphenyl)ethyl)benzamide were then introduced into this solution. The mixture was added to 625 kg of ethanol at 20° C. to 23° C. A thin suspension was obtained, which was stirred at 20° C. to 23° C. for a further 3 h. The product was filtered off and washed with ethanol. After drying, 48 kg of the sodium salt of 5-chloro-2-methoxy-N-(2-(4-methoxy-3-methylaminothiocarbonylaminosulfonylphenyl)ethyl)benzamide in crystal modification 3 were obtained.

EXAMPLE 3

40 kg of 5-chloro-2-methoxy-N-(2-(4-methoxy-3-methylaminothiocarbonylaminosulfonylphenyl)ethyl)benzamide were suspended in a mixture of 80 l of methanol and 136 l of ethanol in an enameled stirring vessel and the temperature was adjusted to 27° C. A solution of 4.7 kg of sodium hydroxide in 58 l of methanol and 3.2 l of water was then metered in in the course of 10 to 15 minutes. The mixture was stirred at 27° C. for 3 h and then cooled to 23° C. After filtration and washing with ethanol, 37.9 kg of the sodium salt of 5-chloro-2-methoxy-N-(2-(4-methoxy-3-methylaminothiocarbonylaminosulfonylphenyl)ethyl)benzamide in crystal modification 1 were obtained.

EXAMPLE 4

11.5 g of 5-chloro-2-methoxy-N-(2-(4-methoxy-3-methylaminothiocarbonylaminosulfonylphenyl)ethyl)benzamide were dissolved in a mixture of 50 ml of methanol and 25 ml of N-methylpyrrolidone at 70° C. in a glass container. The mixture was cooled to 40° C. and a solution of 1.6 g of sodium methoxide in 50 ml of methanol was metered in with stirring. The resulting sodium salt was precipitated by slow addition of 150 ml of diisopropyl ether, filtered off with suction, washed with diisopropyl ether, and dried in vacuo at 60° C. 10.2 g of the sodium salt of 5-chloro-2-methoxy-N-(2-(4-methoxy-3-methyl-aminothiocarbonylaminosulfonylphenyl)ethyl)benzamide in crystal modification 3 were obtained.

EXAMPLE 5

10 g of 5-chloro-2-methoxy-N-(2-(4-methoxy-3-methylaminothiocarbonylaminosulfonylphenyl)ethyl)benzamide were dissolved in 360 ml of tetrahydrofuran at boiling temperature in a glass container. The mixture was allowed to cool to room temperature and was treated with a solution of 0.92 g of sodium hydroxide prills in 20 ml of methanol. The mixture was then cooled to 0° C. and stirred for a further 8 h. A fine precipitate gradually deposited, which was filtered off with suction, washed with tetrahydrofuran, and dried at 60° C. in a vacuum drying oven. 9.6 g of the sodium salt of 5-chloro-2-methoxy-N-(2-(4-methoxy-3-methylaminothiocarbonylaminosulfonyl-phenyl)ethyl)benzamide in crystal modification 3 were obtained.

EXAMPLE 6

4.4 g of sodium hydroxide were stirred in 240 ml of ethanol at about 60° C. until a clear solution was formed. 47.2 g of 5-chloro-2-methoxy-N-(2-(4-methoxy-3-methylaminothiocarbonylaminosulfonylphenyl)ethyl)benzamide were added at 53° C. and the mixture was stirred. The mixture was allowed to cool in the course of 30 minutes and was stirred for a further 1.5 h at 23° C. It was then cooled to 0° C. to 5° C. and stirred again for 40 minutes. The precipitated product was filtered off, washed with 50 ml of ethanol, and dried. 48.06 g of the sodium salt of 5-chloro-2-methoxy-N-(2-(4-methoxy-3-methylaminothio-carbonylaminosulfonylphenyl)ethyl)benzamide in crystal modification 4 were obtained.

EXAMPLE 7

40 kg of 5-chloro-2-methoxy-N-(2-(4-methoxy-3-methylaminothiocarbonylaminosulfonylphenyl)ethyl)benzamide were added to 80 l of methanol in a stirring vessel and the temperature was adjusted to 15° C. to 25° C. A solution of 4.7 kg of sodium hydroxide in 58 l of methanol and 3.2 l of water was then added. The mixture was stirred for 1 h at 27° C., then heated to boiling, and kept for 16 h at boiling temperature. It was then cooled to 6° C. and the product was isolated by filtration. The sodium salt of 5-chloro-2-methoxy-N-(2-(4-methoxy-3-methyl-aminothiocarbonylaminosulfonylphenyl)ethyl)benzamide in crystal modification 2 was obtained.

EXAMPLE 8

10 g of the sodium salt of 5-chloro-2-methoxy-N-(2-(4-methoxy-3-methylaminothiocarbonylaminosulfonylphenyl)ethyl)benzamide in crystal modification 3 were suspended in 50 ml of methanol. The mixture was heated to boiling and stirred for a further 20 h at boiling temperature. It was then cooled to 5° C. and the product was isolated by filtration. The sodium salt of 5-chloro-2-methoxy-N-(2-(4-methoxy-3-methylaminothiocarbonylaminosulfonylphenyl)ethyl)benzamide in crystal modification 2 was obtained.

EXAMPLE 9

10 g of the sodium salt of 5-chloro-2-methoxy-N-(2-(4-methoxy-3-methylaminothiocarbonylaminosulfonylphenyl)ethyl)benzamide were suspended in 200 ml of methanol in a pressure-resistant reactor. The reactor was sealed and heated at 78° C. for 8 h. It was then cooled to 0° C. to 10° C. and the product was isolated by filtration. The sodium salt of 5-chloro-2-methoxy-N-(2-(4-methoxy-3-methylaminothiocarbonylaminosulfonylphenyl)ethyl)benzamide in crystal modification 2 was obtained.

EXAMPLE 10

10 g of the sodium salt of 5-chloro-2-methoxy-N-(2-(4-methoxy-3-methylaminothiocarbonylaminosulfonylphenyl)ethyl)benzamide in crystal modification 4 were suspended in 200 ml of ethanol in a pressure-resistant reactor. The reactor was sealed and heated at 92° C. for 18 h. The mixture was then cooled to 4° C. and the product was isolated by filtration. The sodium salt of 5-chloro-2-methoxy-N-(2-(4-methoxy-3-methylaminothiocarbonylaminosulfonylphenyl)ethyl)benzamide in crystal modification 3 was obtained.

EXAMPLE 11

Methanol-moist 5-chloro-2-methoxy-N-(2-(4-methoxy-3-methylaminothiocarbonylaminosulfonylphenyl)ethyl)benzamide (with a dry weight of 72.5 kg) was added to 145 l of methanol in an enameled stirring vessel and suspended at 27° C. A solution of 8.5 kg of sodium hydroxide platelets in 143 l of methanol was then added. The vessel contents were stirred at 27° C. for 3 h. The mixture was then cooled to 10° C. and the sodium salt was isolated by filtration. The isolated product was washed with cold methanol and dried in vacuo. 68 kg of the sodium salt of 5-chloro-2-methoxy-N-(2-(4-methoxy-3-methylaminothiocarbonylamino-sulfonylphenyl)ethyl)benzamide in crystal modification 3 were obtained.

X-ray diffraction investigations

The X-ray diffraction diagrams of the crystal modifications according to the invention were produced from crystal powders in transmission on a STADIP two-circle diffractometer from Stoe (Darmstadt, Germany) using Cu $K_{\alpha 1}$ radiation. Below, the X-ray reflections are listed in the form that the diffraction angle 2Theta (=2θ) in degrees (°) is indicated at which the X-ray diffraction reflection occurs, and behind it in brackets the relative intensity of the reflection in percent of the intensity of the strongest reflection whose intensity was set equal to 100%. The relative intensities are rounded to a multiple of 5% of the intensity of the strongest reflection. These rounded relative intensities also form the basis for the division into strong and medium-strong X-ray reflections carried out above and in the claims. The diffraction angles are rounded to a multiple of 0.050.

X-Ray reflections of crystal modification 1 (2Theta (°) (relative intensity (%)))
7.10° (20%), 8.95° (100%), 9.40° (10%), 11.35° (25%), 12.15° (25%), 13.00° (10%), 15.40° (35%), 17.95° (5%), 18.85° (5%), 20.00° (10%), 21.40° (10%), 21.90° (10%), 22.80° (20%), 23.00° (35%), 23.50° (35%), 24.10° (10%), 24.50° (15%), 26.85° (5%), 27.70° (5%), 30.80° (5%), 32.25° (5%).

X-Ray reflections of crystal modification 2 (2Theta (°) (relative intensity (%)))
7.15° (95%), 9.90° (45%), 11.10° (90%), 11.35° (10%), 13.35° (20%), 13.80° (45%), 14.00° (25%), 14.35° (10%), 14.90° (30%), 15.40° (10%), 16.30° (15%), 16.50° (10%), 17.00° (15%), 17.30° (5%), 17.95° (5%), 18.95° (30%), 19.85° (25%), 21.20° (10%), 21.60° (25%), 22.20° (10%), 22.55° (20%), 22.85° (70%), 23.10° (100%), 23.90° (45%), 24.30° (25%), 25.45° (20%), 26.80° (65%), 27.15° (25%), 27.85° (5%), 28.25° (25%), 28.35° (25%), 28.70°

(10%), 28.95° (20%), 29.50° (5%), 30.10° (10%), 31.70° (5%), 32.30° (10%), 33.80° (5%).

X-Ray reflections of crystal modification 3 (2Theta (°) (relative intensity (%)))
8.35° (80%), 9.20° (5%), 9.65° (5%), 11.75° (100%), 11.95° (70%), 12.45° (20%), 12.90° (5%), 13.70° (65%), 14.15° (5%), 15.80° (45%), 16.45° (40%), 18.10° (30%), 18.45° (40%), 18.80° (15%), 19.35° (30%), 19.45° (25%), 19.75° (70%), 20.55° (15%), 20.90° (55%), 21.40° (25%), 21.90° (70%), 22.20° (30%), 23.00° (35%), 23.85° (10%), 24.05° (10%), 24.90° (90%), 25.15° (40%), 25.45° (25%), 25.90° (15%), 26.40° (65%), 27.55° (15%), 28.00° (5%), 28.45° (55%), 29.10° (15%), 29.55° (15%), 29.80° (5%), 30.15° (45%), 30.50° (5%), 31.25° (10%), 31.45° (5%), 31.70° (10%), 33.80° (10%).

X-Ray reflections of crystal modification 4 (2Theta (°) (relative intensity (%)))
6.30° (10%), 7.40° (25%), 8.70° (65%), 8.95° (80%), 9.45° (10%), 10.25° (10%), 10.45° (20%), 10.85° (90%), 11.40° (5%), 12.20° (65%), 12.60° (45%), 14.10° (5%), 14.75° (5%), 15.65° (35%), 16.30° (45%), 16.90° (15%), 17.75° (25%), 18.10° (20%), 18.80° (15%), 19.20° (25%), 20.50° (70%), 20.80° (10%), 21.30° (50%), 21.85° (15%), 22.25° (15%), 22.90° (25%), 23.35° (15%), 23.85° (100%), 24.60° (40%), 25.35° (20%), 25.60° (20%), 25.95° (30%), 26.55° (15%), 27.15° (10%), 27.45° (15%), 27.95° (10%), 28.70° (20%), 29.25° (5%), 29.40° (5%), 30.30° (5%), 30.95° (5%), 32.30° (10%), 33.40° (5%).

Hygroscopicity Investigations

The water vapor sorption of the crystal modifications according to the invention was investigated at a temperature of 25° C. on substance samples of about 12 to 16 mg using a DVS-1 Dynamic Vapour Sorption Analyser from Surface Measurement Systems. The measurements were carried out in a nitrogen atmosphere whose relative humidity was altered stepwise. The weight of the sample was recorded at each relative humidity after establishment of the equilibrium, which is when a change in weight of the sample no longer took place. For a series of increasing relative humidities, the water contents of the substance samples, which were determined from the change in weight compared with the starting weights, are indicated in percent.

Crystal Modification 1

| Relative humidity (%) | 18.4 | 39.6 | 61.0 | 81.1 | 91.0 |
|---|---|---|---|---|---|
| Water content (%) | 0.30 | 0.65 | 1.39 | 2.04 | 5.72 |

Crystal Modification 2

| Relative humidity (%) | 18.5 | 39.9 | 61.5 | 81.9 | 91.7 |
|---|---|---|---|---|---|
| Water content (%) | 0.04 | 0.06 | 0.08 | 0.10 | 0.13 |

Crystal Modification 3

| Relative humidity (%) | 18.7 | 40.1 | 61.4 | 81.3 | 91.0 |
|---|---|---|---|---|---|
| Water content (%) | 0.06 | 0.21 | 0.38 | 0.65 | 0.79 |

Solubility Investigations

Crystal Modification 1

The substance was introduced with stirring into 2.0 ml of water at room temperature in portions of 50 to 100 mg. It went into solution in the course of a few minutes with initial clumping. In this way, a total of up to 500 mg of substance could be dissolved in 2 ml of water at 20° C to 25° C.

Crystal Modification 2

100 mg of the substance were introduced into 2.0 ml of water, a readily stirrable suspension being formed. Even after stirring at 20° C. to 25° C. for 2 h, a clear solution was still not formed. On warming the suspension to 35° C. to 37° C., the substance went into solution within 20 minutes. On cooling to 20° C. to 25° C., the substance remained clearly dissolved.

Crystal Modification 3

The substance was introduced with stirring into 2.0 ml of water at room temperature in portions of 50 to 100 mg. After introduction, the substance was initially present as a granular, readily stirrable solid that then went into solution in the course of a few minutes. In this way, a total of up to 360 mg of substance could be dissolved in 2 ml of water at 20° C. to 25° C.

Crystal Modification 4

The substance was introduced with stirring into 2.0 ml of water at room temperature in portions of 50 to 100 mg. It went into solution in the course of a few minutes with initial clumping. In this way, a total of up to 620 mg of substance could be dissolved in 2 ml of water at 20° C. to 25° C.

What is claimed is:

1. A crystalline sodium salt of 5-chloro-2-methoxy-N-(2-(4-methoxy-3-methylaminothiocarbonylaminosulfonylphenyl)ethyl)benzamide.

2. The crystal modification 1 of the sodium salt of 5-chloro-2-methoxy-N-(2-(4-methoxy-3-methylaminothiocarbonylaminosulfonylphenyl)ethyl)benzamide of claim 1, which has X-ray reflections at the following diffraction angles 2Theta (in°) in the X-ray diffraction diagram using Cu $K_{\alpha 1}$ radiation:

strong X-ray reflections: 8.95°;

medium-strong X-ray reflections: 7.10°, 11.35°, 12.15°, 15.40°, 22.80°, 23.00°, 23.50°.

3. The crystal modification 2 of the sodium salt of 5-chloro-2-methoxy-N-(2-(4-methoxy-3-methylaminothiocarbonylaminosulfonylphenyl)ethyl)benzamide of claim 1, which has X-ray reflections at the following diffraction angles 2Theta (in°) in the X-ray diffraction diagram using Cu $K_{\alpha 1}$ radiation:

strong X-ray reflections: 7.15°, 11.10°, 22.85°, 23.10°, 26.80°;

medium-strong X-ray reflections: 7.15°, 11.10°, 22.85°, 23.10°, 26.80°;

medium-strong X-ray reflections: 9.90°, 13.35°, 13.80°, 14.00°, 14.90°, 18.95°, 19.85°, 21.60°, 22.55°, 23.90°, 24.30°, 25.45°, 27.15°, 28.25°, 28.35°, 28.95°.

4. The crystal modification 3 of the sodium salt of 5-chloro-2-methoxy-N-(2-(4-methoxy-3-methylaminothiocarbonylaminosulfonylphenyl)ethyl)benzamide of claim 1, which has X-ray reflections at the following diffraction angles 2Theta (in°) in the X-ray diffraction diagram using Cu $K_{\alpha 1}$ radiation:

strong X-ray reflections: 8.35°, 11.75°, 11.95°, 13.70°, 19.75°, 20.90°, 21.90°, 24.90°, 26.40°, 28.45°;

medium-strong X-ray reflections: 12.45°, 15.80°, 16.45°, 18.10°, 18.45°, 19.35°, 19.45°, 21.40°, 22.20°, 23.00°, 25.15°, 25.45°, 30.15°.

5. The crystal modification 4 of the sodium salt of 5-chloro-2-methoxy-N-(2-(4-methoxy-3-methylaminothiocarbonylaminosulfonylphenyl)ethyl)benzamide of claim 1, which has X-ray reflections at the following diffraction angles 2Theta (in°) in the X-ray diffraction diagram using Cu $K_{\alpha 1}$ radiation:

strong X-ray reflections: 8.70°, 8.95°, 10.85°, 12.20°, 20.50°, 21.30°, 23.85°;

medium-strong X-ray reflections: 7.40°, 10.45°, 12.60°, 15.65°, 16.30°, 17.75°, 18.10°, 19.20°, 22.90°, 24.60°, 25.35°, 25.60°, 25.95°, 28.70°.

6. A process for the preparation of the sodium salt of 5-chloro-2-methoxy-N-(2-(4-methoxy-3-methyl-aminothiocarbonylaminosulfonylphenyl)ethyl)benzamide of claim 1, comprising reacting 5-chloro-2-methoxy-N-(2-(4-methoxy-3-methylaminothiocarbonylaminosulfonyl-phenyl)ethyl)benzamide with a basic sodium compound in a solvent or solvent mixture.

7. A process for the preparation of crystal modification 1 of the sodium salt of 5-chloro-2-methoxy-N-(2-(4-methoxy-3-methylaminothiocarbonylaminosulfonylphenyl)-ethyl) benzamide of claim 2, comprising reacting 5-chloro-2-methoxy-N-(2-(4-methoxy-3-methylaminothiocarbonyl-aminosulfonylphenyl)ethyl)benzamide with a basic sodium compound in a mixture of methanol and ethanol or a mixture of methanol, ethanol, and water and working at temperatures from about −10° C. to about +40° C.

8. A process for the preparation of crystal modification 2 of the sodium salt of 5-chloro-2-methoxy-N-(2-(4-methoxy-3-methylaminothiocarbonylaminosulfonylphenyl)-ethyl) benzamide of claim 3, comprising reacting 5-chloro-2-methoxy-N-(2-(4-methoxy-3-methylaminothio-carbonylaminosulfonylphenyl)ethyl)benzamide with a basic sodium compound in methanol or a mixture of methanol and water and heating the mixture to a temperature from about +40° C. to about +80° C.

9. A process for the preparation of crystal modification 3 of the sodium salt of 5-chloro-2-methoxy-N-(2-(4-methoxy-3-methylaminothiocarbonylaminosulfonylphenyl)-ethyl) benzamide of claim 4, comprising reacting 5-chloro-2-methoxy-N-(2-(4-methoxy-3-methylaminothio-carbonylaminosulfonylphenyl)ethyl)benzamide with a basic sodium compound in methanol, in a mixture of methanol and water, in tetrahydrofuran, in dimethylformamide, in N-methylpyrrolidone, or in dimethyl sulfoxide, or in a mixture of methanol and one or more of the solvents tetrahydrofuran, dimethylformamide, N-methylpyrrolidone, and dimethyl sulfoxide and working at temperatures from about −10° C. to about +40° C.

10. A process for the preparation of crystal modification 4 of the sodium salt of 5-chloro-2-methoxy-N-(2-(4-methoxy-3-methylaminothiocarbonylaminosulfonyl-phenyl)-ethyl)benzamide of claim 5, comprising reacting 5-chloro-2-methoxy-N-(2-(4-methoxy-3-methyl-aminothiocarbonylaminosulfonylphenyl)ethyl)benzamide with a basic sodium compound in ethanol or a mixture of ethanol and water and working at temperatures from about −10° C. to about +40° C.

11. A process for the preparation of crystal modification 2 of the sodium salt of 5-chloro-2-methoxy-N-(2-(4-methoxy-3-methylaminothiocarbonylaminosulfonylphenyl)-ethyl) benzamide of claim 3, comprising heating crystal modification 1 of crystal modification 3 of the sodium salt of 5-chloro-2-methoxy-N-(2-(4-methoxy-3-methyl-aminothiocarbonylaminosulfonylphenyl)ethyl)benzamide to a temperature from about +40° C. to about +80° C. in methanol or a mixture of methanol and water.

12. A process for the preparation of crystal modification 3 of the sodium salt of 5-chloro-2-methoxy-N-(2-(4-methoxy-3-methylaminothiocarbonylaminosulfonyl-phenyl)-ethyl)benzamide of claim 4, comprising heating crystal modification 4 of the sodium salt of 5-chloro-2-methoxy-N-(2-(4-methoxy-3-methylaminothiocarbonyl-aminosulfonylphenyl)ethyl)benzamide to a temperature from about +75° C. to about +100° C. in ethanol or a mixture of ethanol and water.

13. A product prepared by the process of claim 7.

14. A product prepared by the process of claim 8.

15. A product prepared by the process of claim 9.

16. A product prepared by the process of claim 10.

17. A product prepared by the process of claim 11.

18. A product prepared by the process of claim 12.

19. A pharmaceutical composition, comprising at least one crystalline sodium salt of 5-chloro-2-methoxy-N-(2-(4-methoxy-3-methylaminothiocarbonylaminosulfonylphenyl) ethyl)benzamide of claim 1, and a pharmaceutically tolerable carrier.

20. A pharmaceutical composition, comprising at least one crystalline sodium salt of 5-chloro-2-methoxy-N-(2-(4-methoxy-3-methylaminothiocarbonylaminosulfonylphenyl) ethyl)benzamide of claim 2, and a pharmaceutically tolerable carrier.

21. A pharmaceutical composition, comprising at least one crystalline sodium salt of 5-chloro-2-methoxy-N-(2-(4-methoxy-3-methylaminothiocarbonylaminosulfonylphenyl) ethyl)benzamide of claim 3, and a pharmaceutically tolerable carrier.

22. A pharmaceutical composition, comprising at least one crystalline sodium salt of 5-chloro-2-methoxy-N-(2-(4-methoxy-3-methylaminothiocarbonylaminosulfonylphenyl) ethyl)benzamide of claim 4, and a pharmaceutically tolerable carrier.

23. A pharmaceutical composition, comprising at least one crystalline sodium salt of 5-chloro-2-methoxy-N-(2-(4-methoxy-3-methylaminothiocarbonylaminosulfonylphenyl) ethyl)benzamide of claim 5, and a pharmaceutically tolerable carrier.

24. A method for treating or preventing cardiac arrhythmias, ischemic conditions of the heart, or weakened myocardial contractile force, comprising administering to a patient in need thereof an effective amount of at least one crystalline sodium salt of 5-chloro-2-methoxy-N-(2-(4-methoxy-3-methylaminothiocarbonylaminosulfonylphenyl) ethyl)benzamide of claim 1.

25. A method for preventing sudden cardiac death, comprising administering to a patient in need thereof an effective amount of at least one crystalline sodium salt of 5-chloro-2-methoxy-N-(2-(4-methoxy-3-methylaminothiocarbonyl-aminosulfonylphenyl)ethyl)benzamide of claim 1.

26. A method for improving the cardiac function in heart transplantation, comprising administering to a patient in need thereof an effective amount of at least one crystalline sodium salt of 5-chloro-2-methoxy-N-(2-(4-methoxy-3-methylaminothiocarbonylaminosulfonylphenyl)ethyl) benzamide of claim 1.

27. A method for inhibiting ATP-sensitive potassium channels, comprising administering to a patient in need thereof an effective amount of at least one crystalline sodium salt of 5-chloro-2-methoxy-N-(2-(4-methoxy-3-methylaminothiocarbonylaminosulfonylphenyl)ethyl) benzamide of claim 1.

28. A method for determining or diagnosing the inhibitory action on ATP-sensitive potassium channels, comprising adding to a cell or tissue sample in vitro at least one crystalline sodium salt of 5-chloro-2-methoxy-N-(2-(4-methoxy-3-methylaminothiocarbonylaminosulfonylphenyl) ethyl)benzamide of claim 1.

* * * * *

UNITED STATES PATENT AND TRADEMARK OFFICE
CERTIFICATE OF CORRECTION

PATENT NO. : 6,723,751 B1
DATED : April 20, 2004
INVENTOR(S) : Heinrich Christian Englert et al.

It is certified that error appears in the above-identified patent and that said Letters Patent is hereby corrected as shown below:

Title page,
Item [54], Title, "CARBONYLAMINOSULFONYLPENYL)" should read
-- CARBONYLAMINOSULFONYLPHENYL --.

Column 20,
Lines 47-48, delete "medium-strong X-ray reflections: 7:15°, 11.10°, 22.85°, 23.10°, 26.80°;".

Column 21,
Line 17, 26, 34 and 55, "3-methylaminothiocarbonylaminosulfonylphenyl)-ethyl)" should read
-- 3-methylaminothiocarbonylaminosulfonylphenyl)ethyl) --.
Line 47 and 65, "phenyl)-ethyl)benzamide" should read -- phenyl)ethyl)benzamide --.

Signed and Sealed this

Twenty-eighth Day of September, 2004

JON W. DUDAS
*Director of the United States Patent and Trademark Office*